(12) United States Patent
Bertolote et al.

(10) Patent No.: US 12,329,589 B2
(45) Date of Patent: Jun. 17, 2025

(54) IMPLANTABLE MEDICAL DEVICES WITH INSERTABLY REMOVABLE ELEMENTS

(71) Applicant: Wyss Center for Bio and Neuro Engineering, Geneva (CH)

(72) Inventors: Tiago Bertolote, Le Grand Saconnex (CH); Christopher D. Gongora, Lyons, CO (US); Dana D. Tompkins, Frederick, CO (US); Claude Clément, Sigtuna (SE)

(73) Assignee: WYSS CENTER FOR BIO AND NEURO ENGINEERING, Geneva (CH)

( * ) Notice: Subject to any disclaimer, the term of this patent is extended or adjusted under 35 U.S.C. 154(b) by 194 days.

(21) Appl. No.: 17/155,249

(22) Filed: Jan. 22, 2021

(65) Prior Publication Data
US 2021/0228310 A1 Jul. 29, 2021

Related U.S. Application Data

(60) Provisional application No. 63/131,595, filed on Dec. 29, 2020, provisional application No. 62/964,918, filed on Jan. 23, 2020.

(51) Int. Cl.
*A61B 90/00* (2016.01)
*A61M 39/02* (2006.01)
(Continued)

(52) U.S. Cl.
CPC ......... *A61B 90/39* (2016.02); *A61M 39/0247* (2013.01); *A61N 1/05* (2013.01);
(Continued)

(58) Field of Classification Search
CPC .......... A61F 2/30734; A61F 2002/3401; A61F 2002/3403; A61F 2002/3406;
(Continued)

(56) References Cited

U.S. PATENT DOCUMENTS 3,951,154 A * 4/1976 Hartlaub ............ H01R 13/5224
607/37
4,141,752 A * 2/1979 Shipko ................. A61N 1/3752
607/37
(Continued)

FOREIGN PATENT DOCUMENTS

EP 3150121 B1 4/2017
EP 2531100 B1 9/2017
(Continued)

OTHER PUBLICATIONS

"Portion, n.". Oxford English Dictionary, Oxford University Press, Sep. 2023, <https://doi.org/10.1093/OED/4739859019> (Year: 2023).*
(Continued)

*Primary Examiner* — Carrie R Dorna
(74) *Attorney, Agent, or Firm* — Hamilton, Brook, Smith & Reynolds, P.C.

(57) ABSTRACT

An implantable device includes a low-profile housing having a cavity defined in a side thereof, and an element insertably removable with respect to the housing in a direction substantially parallel to a surgical plane of the implantable device. The element has a first portion adapted to be received in the housing cavity. The element further includes a second portion adapted to protrude from the housing upon insertion of the element into the housing cavity. The second portion includes at least one surface adapted for engagement with a surgical instrument for insertion and removal of the element with respect to the housing. A method for servicing the implantable device includes, at an incision proximate an implant location of the implantable device, insertably and removably accessing the element in a direction substantially parallel to a surgical plane of the implantable device.

10 Claims, 5 Drawing Sheets

(51) Int. Cl.
*A61N 1/05* (2006.01)
*A61N 1/36* (2006.01)
*A61N 1/375* (2006.01)
*H04R 25/00* (2006.01)

(52) U.S. Cl.
CPC ..... *A61N 1/36038* (2017.08); *A61N 1/37514* (2017.08); *H04R 25/60* (2013.01); *A61B 2090/3954* (2016.02); *A61B 2090/3966* (2016.02); *A61B 2090/3987* (2016.02); *A61B 2560/0412* (2013.01); *A61M 2039/025* (2013.01); *A61M 2039/0279* (2013.01); *A61M 2039/0291* (2013.01); *A61M 2039/0294* (2013.01); *H04R 2225/67* (2013.01)

(58) Field of Classification Search
CPC ..... A61F 2002/3408; A61F 2002/3432; A61N 1/3752; A61N 1/3758
See application file for complete search history.

(56) References Cited

U.S. PATENT DOCUMENTS

| | | | |
|---|---|---|---|
| 4,566,464 A | 1/1986 | Piccone et al. | |
| 5,374,279 A * | 12/1994 | Duffin, Jr. | A61N 1/3956 607/37 |
| 5,535,097 A * | 7/1996 | Ruben | A61N 1/3752 361/728 |
| 5,951,601 A * | 9/1999 | Lesinski | H04R 25/606 623/10 |
| 6,018,682 A | 1/2000 | Rise | |
| 6,034,295 A * | 3/2000 | Rehberg | A61N 1/05 607/51 |
| 6,572,655 B1 * | 6/2003 | Johnson | A61F 2/34 623/22.36 |
| 6,597,953 B2 | 7/2003 | Boling | |
| 7,676,263 B2 | 3/2010 | Harris et al. | |
| 7,704,282 B2 * | 4/2010 | Disilvestro | A61F 2/32 600/587 |
| 7,787,945 B2 | 8/2010 | Greene | |
| 8,036,736 B2 | 10/2011 | Snyder et al. | |
| 8,118,741 B2 | 2/2012 | Beck-Nielsen | |
| 8,140,150 B2 | 3/2012 | Greene | |
| 8,224,434 B2 | 7/2012 | Greene | |
| 8,290,593 B2 * | 10/2012 | Libbey | A61N 1/3752 607/37 |
| 8,396,557 B2 | 3/2013 | Dilorenzo | |
| 8,543,199 B2 | 9/2013 | Snyder et al. | |
| 8,628,472 B2 | 1/2014 | Beck-Nielsen | |
| 8,849,368 B2 | 9/2014 | Madsen et al. | |
| 8,884,767 B2 | 11/2014 | Kidmose | |
| 9,061,134 B2 | 6/2015 | Askin et al. | |
| 9,232,903 B2 | 1/2016 | Pless et al. | |
| 9,326,726 B2 | 5/2016 | Anning et al. | |
| 9,516,434 B2 | 12/2016 | Björn et al. | |
| 9,526,810 B2 | 12/2016 | Ruppersberg | |
| 9,622,675 B2 | 4/2017 | Leyde et al. | |
| 9,649,049 B2 | 5/2017 | Pless et al. | |
| 10,129,667 B2 | 11/2018 | Gustafsson | |
| 10,413,208 B2 | 9/2019 | Kidmose et al. | |
| 10,433,754 B2 | 10/2019 | Nurmikko et al. | |
| 10,568,574 B2 | 2/2020 | Williams et al. | |
| 2003/0109903 A1 | 6/2003 | Berrang et al. | |
| 2003/0195392 A1 * | 10/2003 | Hamel | A61B 17/3417 600/213 |
| 2004/0032962 A1 * | 2/2004 | Westerkull | H04R 25/606 381/151 |
| 2004/0193228 A1 * | 9/2004 | Gerber | A61N 1/32 607/39 |
| 2006/0184204 A1 * | 8/2006 | He | A61N 1/378 607/2 |
| 2007/0270672 A1 | 11/2007 | Hayter | |
| 2008/0027347 A1 | 1/2008 | Harris et al. | |
| 2008/0027348 A1 | 1/2008 | Harris et al. | |
| 2008/0027515 A1 | 1/2008 | Harris et al. | |
| 2008/0065181 A1 * | 3/2008 | Stevenson | A61B 90/90 607/115 |
| 2008/0082141 A1 * | 4/2008 | Risi | A61N 1/0541 607/57 |
| 2008/0183097 A1 | 7/2008 | Leyde et al. | |
| 2010/0137929 A1 | 6/2010 | Libbey et al. | |
| 2011/0130845 A1 * | 6/2011 | Divoux | A61B 17/1746 623/23.43 |
| 2012/0302856 A1 | 11/2012 | Chang et al. | |
| 2012/0302858 A1 | 11/2012 | Kidmose et al. | |
| 2013/0096366 A1 * | 4/2013 | Bervoets | H04R 25/606 600/25 |
| 2014/0012071 A1 | 1/2014 | Nagl | |
| 2016/0250466 A1 | 9/2016 | Boggs, II et al. | |
| 2017/0035316 A1 | 2/2017 | Kuzniecky et al. | |
| 2017/0078808 A1 | 3/2017 | Kennes | |
| 2017/0203111 A1 | 7/2017 | Pless | |
| 2017/0319092 A1 | 11/2017 | Wendel-mitora | |
| 2017/0319096 A1 | 11/2017 | Kaiser et al. | |
| 2018/0055398 A1 | 3/2018 | Westermann et al. | |
| 2018/0117331 A1 * | 5/2018 | Kuzniecky | A61B 5/686 |
| 2018/0153474 A1 | 6/2018 | Aeschlimann et al. | |
| 2018/0154152 A1 | 6/2018 | Chabrol et al. | |
| 2018/0233849 A1 * | 8/2018 | Montague, Jr. | H01R 13/5219 |
| 2019/0209007 A1 | 7/2019 | D-Urso et al. | |
| 2020/0187861 A1 | 6/2020 | Williams et al. | |
| 2020/0330749 A1 | 10/2020 | Gribetz et al. | |
| 2022/0054822 A1 | 2/2022 | Rickert et al. | |

FOREIGN PATENT DOCUMENTS

| | | |
|---|---|---|
| EP | 3291730 A1 | 3/2018 |
| EP | 3298961 A3 | 4/2018 |
| EP | 2686059 B1 | 5/2019 |
| JP | 2000-508844 A | 7/2000 |
| JP | 2011-514222 A | 5/2011 |
| JP | 2019-165838 A | 10/2019 |
| WO | 97/36457 A1 | 10/1997 |
| WO | 0025668 A1 | 5/2000 |
| WO | 2002007596 A1 | 1/2002 |
| WO | 2006/066577 A1 | 6/2006 |
| WO | 2007150003 A1 | 12/2007 |
| WO | 2008092133 A1 | 7/2008 |
| WO | 2009090110 A1 | 7/2009 |
| WO | 2009/115196 A1 | 9/2009 |
| WO | 2011022418 A1 | 5/2011 |
| WO | 2011091856 A1 | 8/2011 |
| WO | 2013054312 A1 | 4/2013 |
| WO | 2015/130955 A1 | 9/2015 |
| WO | 2016/074974 A1 | 5/2016 |
| WO | 2016086219 A1 | 6/2016 |
| WO | 2016177386 A1 | 11/2016 |
| WO | 2017101977 A1 | 6/2017 |
| WO | 2017196477 A1 | 11/2017 |
| WO | 2018032060 A1 | 2/2018 |
| WO | 2018039732 A1 | 3/2018 |
| WO | 2019/018879 A1 | 1/2019 |
| WO | 2019/200918 A1 | 10/2019 |
| WO | 2019211314 A1 | 11/2019 |
| WO | 2020/046532 A1 | 3/2020 |
| WO | 2020086473 A1 | 4/2020 |
| WO | 2020/160613 A1 | 8/2020 |

OTHER PUBLICATIONS

International Search Report for PCT Application No. PCT/US2021/014520, "Implantable Medical Devices With Insertably Removable Elements," mailed Apr. 21, 2021.

"Tips for HiRes 90K Magnet Removal—Replacement Procedure", Boston Scientific; Oct. 26, 2006.

Vercise Deep Brain Stimulation System Physician Manual; Boston Scientific; 2017.

(56) References Cited

OTHER PUBLICATIONS

J. Duun-Henriksen et al.; "A new era in electroencephalographic monitoring? Subscalp devices for ultra-long-term recordings"; Epilepsia; 2020.

* cited by examiner

431 — AT AN INCISION PROXIMATE AN IMPLANT LOCATION OF THE IMPLANTABLE DEVICE, THE IMPLANTABLE DEVICE COMPRISING A LOW-PROFILE HOUSING HAVING A CAVITY DEFINED IN A SIDE THEREOF AND AN ELEMENT HAVING A FIRST PORTION ADAPTED TO BE RECEIVED IN THE HOUSING CAVITY, INSERTABLY AND REMOVABLY ACCESSING THE ELEMENT IN A DIRECTION SUBSTANTIALLY PARALLEL TO A SURGICAL PLANE OF THE IMPLANTABLE DEVICE

433 — WHEREIN THE CAVITY IS A FIRST CAVITY, THE SIDE IS A FIRST SIDE, THE ELEMENT IS A FIRST ELEMENT, AND THE INCISION IS A FIRST INCISION, AT ONE OR MORE RESPECTIVE SECOND INCISIONS PROXIMATE THE IMPLANT LOCATION OF THE IMPLANTABLE DEVICE, THE LOW-PROFILE HOUSING HAVING ONE OR MORE RESPECTIVE SECOND CAVITIES DEFINED IN THE FIRST SIDE OR IN ONE OR MORE RESPECTIVE SECOND SIDES THEREOF, AND THE IMPLANTABLE DEVICE COMPRISING ONE OR MORE SECOND ELEMENTS HAVING RESPECTIVE FIRST PORTIONS ADAPTED TO BE RECEIVED IN THE HOUSING CAVITY, INSERTABLY AND REMOVABLY ACCESSING THE ONE OR MORE SECOND ELEMENTS IN ONE OR MORE RESPECTIVE SECOND DIRECTIONS SUBSTANTIALLY PARALLEL TO THE SURGICAL PLANE

FIG. 4

IMPLANTABLE MEDICAL DEVICES WITH INSERTABLY REMOVABLE ELEMENTS

RELATED APPLICATIONS

This application claims the benefit of U.S. Provisional Application No. 62/964,918, filed Jan. 23, 2020, and U.S. Provisional Application No. 63/131,595, filed on Dec. 29, 2020. The entire teachings of the above applications are incorporated herein by reference.

BACKGROUND

Implantable medical devices exhibit numerous limitations, including limited implant lifetime during which sensing can be reliably performed.

There is a need for improved implantable medical devices.

SUMMARY

The present disclosure relates to methods, elements, and tools for inserting and removing components to and from implanted devices, via minimally invasive device features and techniques (small incisions) rather than usual surgery.

The present disclosure is directed to medical devices which feature elements that can be inserted into, and removed from, an already implanted medical device through small skin incisions. The elements may be, for example, magnets that cannot remain implanted in case the patient needs to undergo MRI procedures, glucose sensors that degrade over time and need to be replaced, radio-opaque markers, RFID tags, electronic modules, different types of sensors (personalized monitoring), and battery packs. The elements have specific shapes (or specific mechanisms) that allow them to be inserted and removed parallel to the surgical plane of the implanted device, so as to require only minimal incisions. The geometries of the elements serve to anchor them to the implanted device, and also provide features that allow an easier grasping/handling with standard surgical instruments, or alternatively with custom designed instruments.

According to an aspect of the disclosure, there is provided an implantable device comprising a low-profile housing having a cavity defined in a side thereof; and an element insertably removable with respect to the housing in a direction substantially parallel to a surgical plane of the implantable device, the element having a first portion adapted to be received in the housing cavity. The element may further comprise a second portion adapted to protrude from the housing upon insertion of the element into the housing cavity. The second portion may include at least one surface adapted for engagement with a surgical instrument for insertion and removal of the element with respect to the housing.

In some embodiments, the element may include any of a magnet, a battery, a sensor, an electronic module, a radio-opaque marker and an RFID tag.

In some embodiments, the element may include a resorbable material and/or a consumable material.

In some embodiments, the housing and element are composed of biocompatible materials.

In some embodiments, the first portion is adapted to be friction fit into the housing cavity.

In some embodiments, the housing cavity includes a cavity wall and the first portion and the cavity wall are keyed to each other for engagement and alignment.

In some embodiments, the element is insertably removable with respect to the housing via an incision through a skin of a subject, wherein a length of the incision is less than or equal to 20 mm, 10 mm, or 5 mm, or wherein the length of the incision is in a range of 5 mm to 20 mm, 5 mm to 15 mm, or 7 mm to 13 mm.

In some embodiments, the cavity is a first cavity, the side is a first side, and the element is a first element. The device further includes one or more second cavities defined in the first side or in one or more respective second sides of the low-profile housing. The device further includes one or more respective second elements insertably removable with respect to the housing in one or more respective second directions substantially parallel to the surgical plane of the implantable device. The one or more respective second elements have one or more respective first portions adapted to be received in the housing cavity.

According to another aspect of the disclosure, there is provided a method for servicing an implantable device implanted in a subject, wherein the method comprises at an incision proximate an implant location of the implantable device, the implantable device comprising a low-profile housing having a cavity defined in a side thereof and an element having a first portion adapted to be received in the housing cavity and a second portion adapted to protrude from the housing, insertably and removably accessing the element in a direction substantially parallel to a surgical plane of the implantable device.

In some embodiments of the method, the second portion includes at least one surface adapted for engagement with a surgical instrument for insertion and removal of the element with respect to the housing.

In some embodiments of the method, the cavity is a first cavity, the side is a first side, the element is a first element, and the incision is a first incision. The method further includes accessing at one or more respective second incisions proximate the implant location of the implantable device. The low-profile housing can have one or more respective second cavities defined in the first side or in one or more respective second sides thereof. The implantable device can include one or more second elements having respective first portions adapted to be received in the housing cavity. The accessing is particularly insertably and removably accessing the one or more second elements in one or more respective second directions substantially parallel to the surgical plane.

BRIEF DESCRIPTION OF THE DRAWINGS

The foregoing will be apparent from the following more particular description of example embodiments, as illustrated in the accompanying drawings in which like reference characters refer to the same parts throughout the different views. The drawings are not necessarily to scale, emphasis instead being placed upon illustrating embodiments.

FIG. 4 is a flow diagram illustrating an embodiment procedure.

DETAILED DESCRIPTION

A description of example embodiments follows.

Reference will now be made in detail to the present embodiments of the technology, examples of which are illustrated in the accompanying drawings. Similar reference numbers may be used to refer to similar components. However, the description is not intended to limit the present disclosure to particular embodiments, and it should be construed as including various modifications, equivalents, and/or alternatives of the embodiments described herein.

Figure 1:
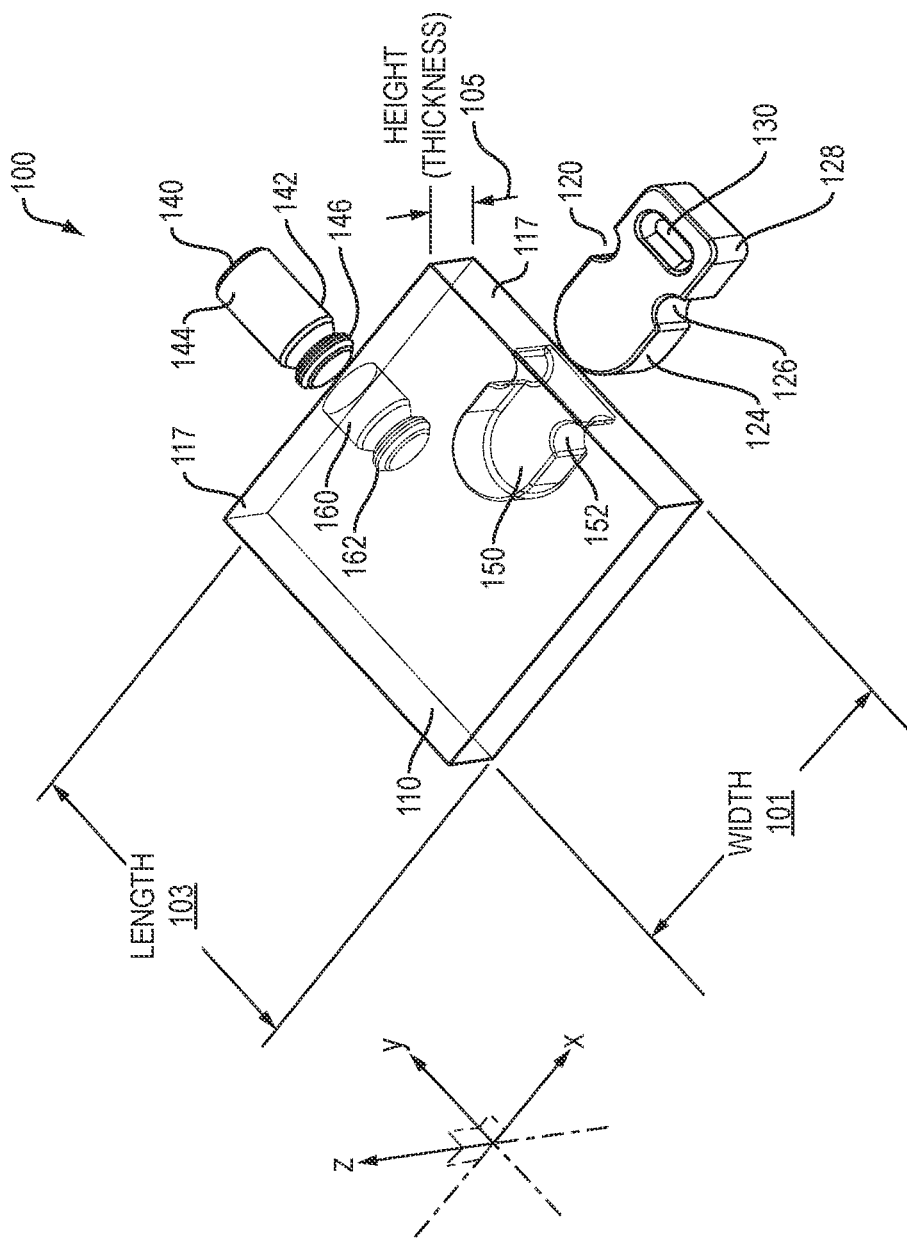
FIG. 1 illustrates a conceptual view of an embodiment of an implantable device, consistent with the disclosure.

FIG. 1 illustrates a conceptual view of an example embodiment of a simplified implantable device 100 which includes a low-profile housing 110. As used herein, a "low-profile housing" is a housing that has a width 101 and length 103 in a surgical plane of the implantable device 100, both of which are greater than a height (thickness) 105 of the device in a direction perpendicular to the surgical plane of the device. A low-profile housing may be relatively flat in various embodiments, as exemplified by the housing 110 and by embodiments described hereinafter in connection with FIGS. 2A-2B and 3. It should also be understood that a "low-profile housing" as used herein is a housing of a size that is suitable for implantation. A low-profile housing allows the device to be implanted subcutaneously, such as between layers of skin or flesh or between bone and skin or other flesh, such as between the skull and skin covering the skull. The low-profile housing may allow the device to be implanted subcutaneously, such as by screwing the device to the skull, while avoiding having to sink the device itself into the skull or requiring any other intrusion into the skull, while still avoiding significant protrusions of the device through the normal contour of the skin, where the normal contour of the skin is that which would be expected in the absence of the implanted device. Bumps under the skin that indicate a presence of the device may be substantially avoided. Toward that end, in some embodiments, the height (thickness) 105 may be less than or equal to 10 mm, such as in the range of 2 mm to 10 mm. More preferably, the height 105 may be less than or equal to 6 mm, such as in the range of 2 mm to 6 mm. Even more preferably, the height 105 may be less than or equal to 5 mm, such as in the range of 2 mm to 5 mm. Still more preferably, the height may be less than or equal to 3 mm, such as in the range of 2 mm to 3 mm. In some particular subcutaneously implantable embodiments used for neurological applications applied to the skull, the height may be in a range of 2 mm to 5 mm. However, it should be understood that other embodiments can be applied to other body parts not in the vicinity of the skull.

A "surgical plane" as used herein should be understood as consistent with the usage of this term in the field of surgery, and specifically in the field of neurological implant surgery. For the implantable device 100 in FIG. 1, the surgical plane of the device 100 is the XY plane illustrated in FIG. 1. Arbitrarily, the width 101 is measured parallel to the X axis, the length 103 is measured in a direction parallel to the Y axis, and the height (thickness) 105 is measured in a direction parallel to the Z axis. In some particular subcutaneously implantable embodiments used for neurological applications applied to the skull, the surgical plane may be substantially parallel to the portion of the skull to which the implanted device is applied. In this usage, "substantially parallel" can indicate that the XY surgical plane is within 20 degrees of perfectly parallel to the skull, or, more preferably, within 10 degrees of perfectly parallel to the skull.

The conceptual view of FIG. 1 illustrates two example types of respective, insertably removable elements 120, 140. Element 120 has a first portion 124 and a second portion 128. The first portion 124 is configured to be received in a cavity 150 that is defined in a first side 117 in the housing 110. The housing cavity 150 includes a cavity wall 152, which is keyed for alignment and engagement with opposing locking indents 126 of the first portion 124. The second portion 128 of the element 120 is configured to protrude from the housing 110 upon insertion of the first portion 124 of element 120 into the housing cavity 150. The second portion 128 includes a detent 130 configured for engagement with a surgical instrument (not shown) adapted for insertion and removal of the element 120 with respect to the housing 110.

Element 140 is generally cylindrical in shape and has a respective first portion 142 and a respective second portion 144. The first portion 142 is configured to be received in a cavity 160 that is defined in another, second side 117 in the housing 110. The housing cavity 160 includes a cavity wall 162 that is defined and cylindrically keyed for alignment and engagement with annular locking indent 146 of the first portion 124. As an alternative to the keying-based alignment, engagement, and locking illustrated in FIG. 1 for the first portions 124 and 142, or in addition, in other embodiments the first portions 124 and 142 and the respective housing cavities 150 and 160 may be adapted for a friction-fit-based alignment, engagement, and locking. The second portion 144 of the element 140 is configured to protrude from the housing 110 upon insertion of the first portion 142 of element 140 into the housing cavity 160. Insertion and removal of the element 140 with respect to the housing 110 may be achieved by gripping the second portion 144 with a surgical instrument or by hand.

It should be understood that embodiments are not limited to one cavity per side of the housing. In general, any number of respective cavities and corresponding respective insertably removable elements, such as two or more insertably removable elements, may be provided for a given side 117 of the housing. Furthermore, a given embodiment device may include either one or two or more cavities and corresponding insertably removable elements distributed among one side 117, two respective sides 117, or more respective sides of the device. It should also be understood that embodiments are not limited to any particular housing shape. While the housing 110 has a generally rectangular profile in the surgical plane (parallel to the XY plane), a housing in other embodiments may have another shape, or may be characterized by multiple shapes of different portions thereof, including irregular shapes. In one example, a housing 210 described hereinafter in connection with FIGS. 2A-2B includes a semicircular portion encapsulating a coil, a substantially rectangular portion encapsulating electronics, and various protrusions at sides thereof that are useful for securing the device to a subject skull, forming cavities that can accommodate insertably removable elements, and protecting leads that extend through the housing.

Figure 2A:
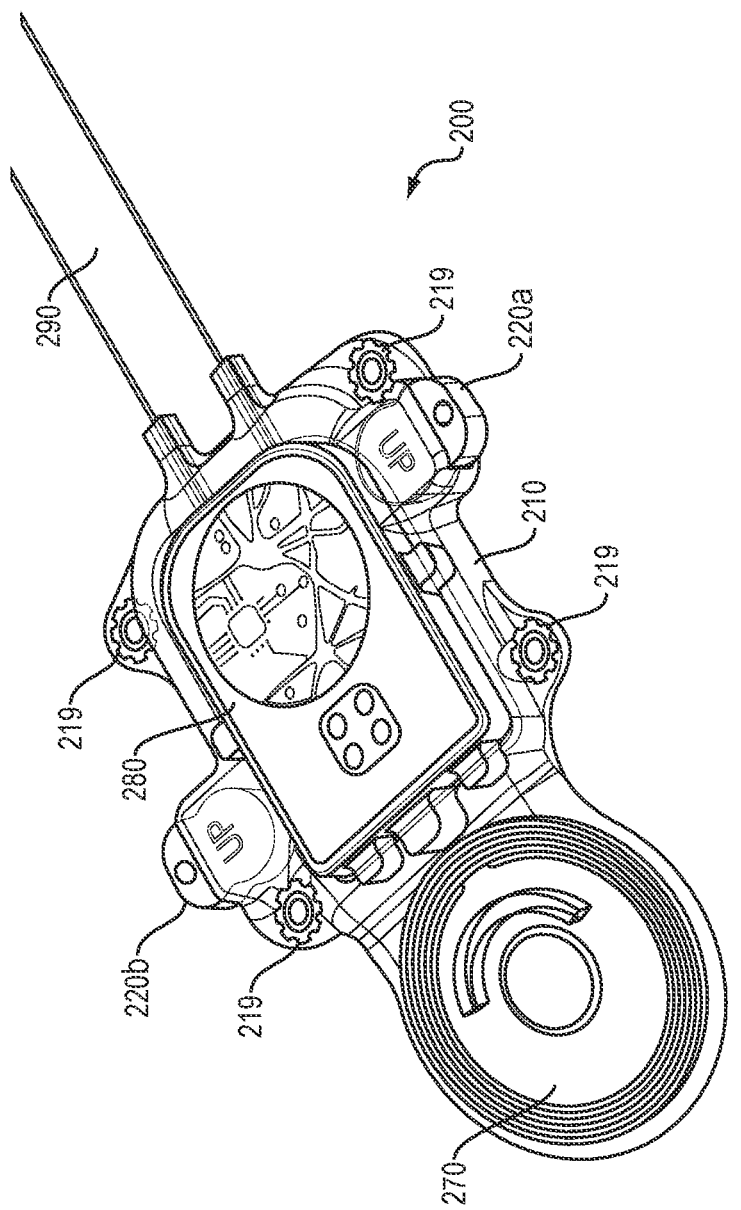
FIGS. 2A and 2B illustrate a schematic view of an embodiment of an implantable device with elements inserted and removed, consistent with the disclosure.
Figure 2B:
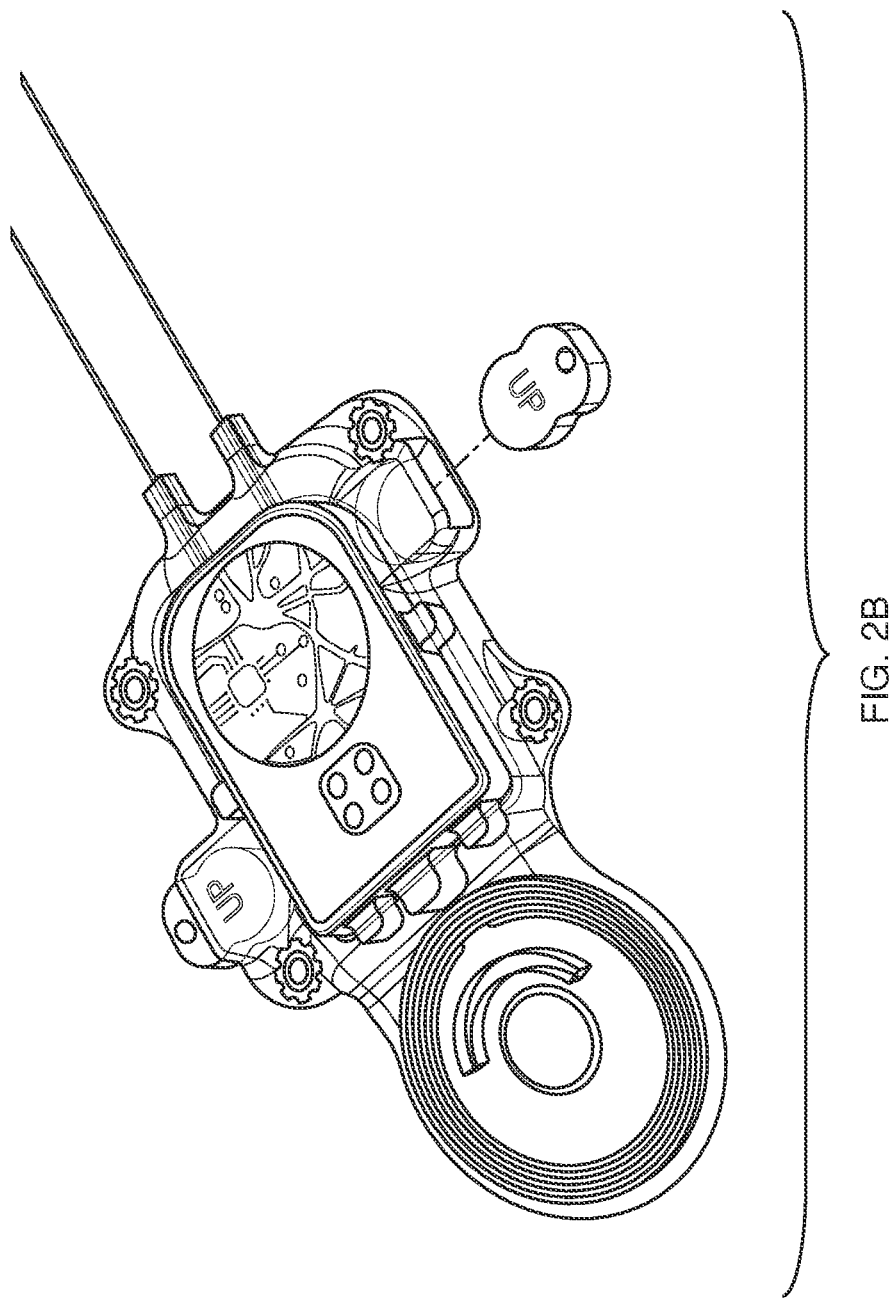
Figure 3:
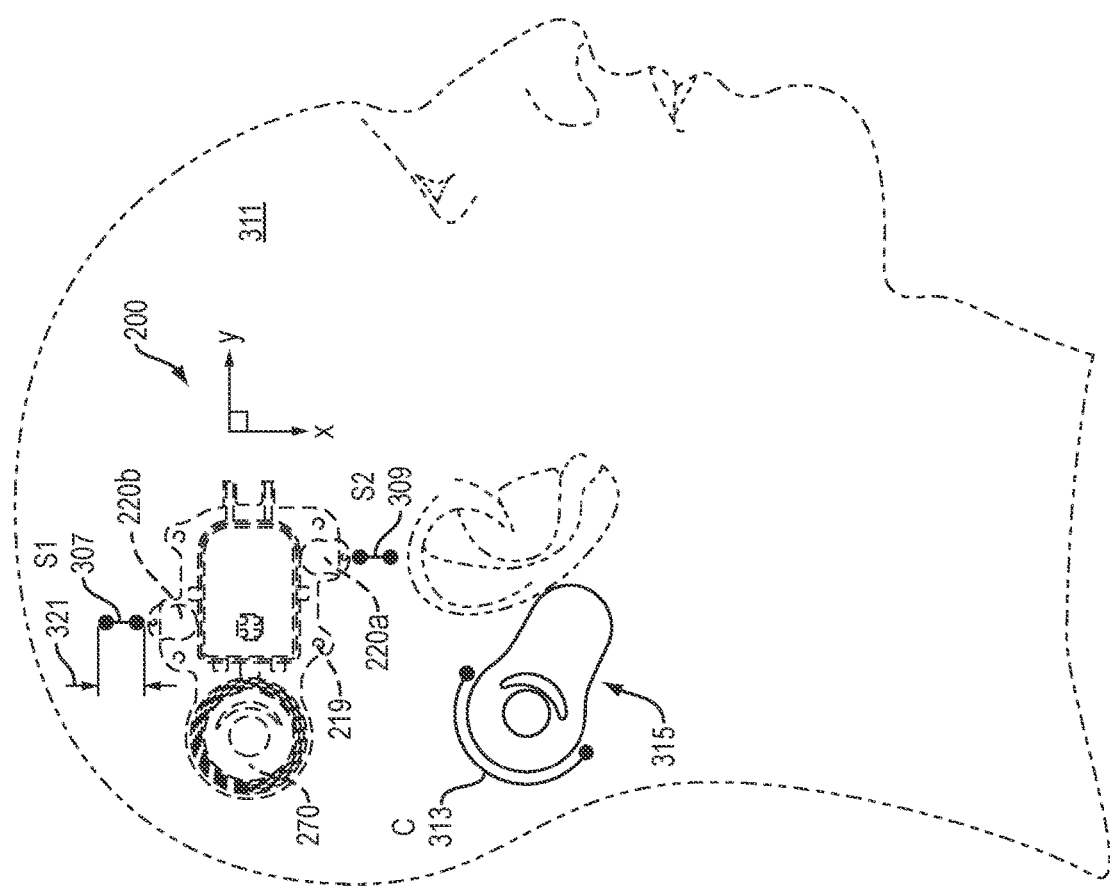
FIG. 3 illustrates a pictorial view of a subject with the implantable device of FIGS. 2A and 2B and a cochlear implant device.

Further, because a housing according to embodiments may be part of an entire device that forms part of an implantable device, the housing may be referred to as "implantable housing", a "surgically implantable housing", and the like. In greater particular, the embodiment described hereinafter in connection with FIGS. 2A-2B and 3 is configured for neurological functions, to be implanted subcutaneously and secured to a skull; consequently, the housing 210 of that embodiment may be described using the terms "neurological, subcutaneously, surgically implantable housing" and similar terms. In addition, it should be understood that a "side" of a housing in other embodiments need not be planar, as are the sides 117 of the housing 110. Sides may generally be of any shape or orientation that can provide space for a cavity that can accommodate any insertably removable element, as will be understood in greater measure by reference to example FIGS. 2A-2B.

For both example elements, insertion and removal occur in respective directions, both of which are parallel to a surgical plane of the housing. These respective directions are parallel to the X axis for the element 120 and parallel the Y axis for the element 140. However, in other embodiments, the insertion and removal occur in a direction that is only substantially parallel to the surgical plane of the housing. In this usage in relation to insertion and removal, "substantially parallel" to the surgical plane means that the insertion and removal are in a direction that is within 45 degrees of the surgical plane. In order to enable insertion and removal in a direction that is not perfectly parallel but still substantially parallel to the surgical plane, within 45 degrees of the surgical plane, the housing cavities 150 and 160 can be oriented at a corresponding angle with respect to the surgical plane, instead of parallel to the surgical plane as illustrated in FIG. 1. In more preferable embodiments, the insertion and removal are in a direction that is within 20 degrees of the surgical plane. Still more preferably, the insertion and removal can be in a direction that is within 10 degrees of the surgical plane. Nonetheless, as illustrated and described in connection with FIGS. 1 and 2A-2B, it is most preferable for the insertion and removal to be in a direction that is parallel to the surgical plane. "Substantially parallel" insertion and removal enable servicing the elements with minimal invasiveness and in a manner that avoids significant protrusions of the device through the normal contour of the skin, where the normal contour of the skin is the contour that would be expected in the absence of the implanted device.

As used herein, "insert", "insertion", "insertably", "insertable", and the like in relation to the insertably removable elements denotes insertion into the housing of the device, under the skin, without leads or other connections to the elements protruding through skin after an insertion procedure is complete. Thus, as used herein, "insert", "insertion", "insertably", "insertable", and the like may be understood to mean "connectorlessly insert", "connectorless insertion", "connectorlessly insertably", "connectorlessly insertable", and the like.

The ability to insert and remove elements substantially parallel to the device surgical plane offers an advantage, because installation, removal, or replacement of elements only requires small incisions beside the implant location, rather than requiring skin flap lifting to expose the top of the implant, as done in cochlear implant magnet removal. Thus, the approach of the present disclosure provides for a minimally invasive implantable device. In particular, servicing modular, replaceable elements in the implantable devices may be made minimally invasive. In one example, an insertably removable element may include a magnet that is used for alignment of a coil that is part of the device, such as the induction coil 270 illustrated in FIG. 2A, with a coil that is external to the device. While such a magnet may be useful for alignment, the magnet can interfere with an MRI procedure. Embodiments described herein permit minimally invasive removal and reinstallation of an insertably removable magnet element as needed. In other examples, insertably removable elements can include batteries or sensors that require replacement periodically, such as a glucose sensor. Replacement of such sensors, also, can be minimally invasive as part of embodiment devices. Other exemplary types of insertably removable elements within the scope of embodiments are described herein. However, the scope of what is encompassed by insertably removable elements is not limited to these examples. Insertably removable elements as described herein may be electrically coupled to an electrical circuit encompassed by the housing for power flow or communication between the housing and the elements.

It should be understood that a variety of shapes besides those shown in FIG. 1 can be envisioned as insertably removable elements. In addition, other locking/engagement mechanisms can be employed, including press fitting the elements with respect to the housing.

By making the elements insertably removable, it is envisioned that different modules can add features to an implanted device without the need to replace the entire device.

FIGS. 2A and 2B illustrate a schematic view of an example embodiment of an implantable device 200 with elements inserted (FIG. 2A) and partially removed (FIG. 2B). The device 200 includes a low-profile housing 210 that houses several components including induction coil 270 and electronic circuits 280 (inside housing). Electronic circuits as described herein may also be referred to as one or more "electronic modules." Leads 290 connect to the sensor 280. The housing includes skull attachment features 219 for securing the housing to a skull of a subject. In this embodiment, the skull attachment features 219 are holes for screwing the device to the skull. In other embodiments, other types of attachment features optionally may be provided for attachment to a different bone or for securing the device in other subcutaneous locations.

In some embodiments, the electronic circuits 280 can include a processor, such as a microprocessor, that receives and processes information received from one or more insertably removable elements. In some embodiments, the electronic circuits 280 can include a processor that sends information or instructions to one or more insertably removable elements. Instructions may include actuating the one or more elements to perform a function. In some embodiments, the electronic circuits 280 include a communication interface that is configured to send information to a receiver outside of the housing, device, and subject. In some embodiments, the electronic circuits 280 include a communication interface that is configured to receive information, commands, or other instructions from a transmitter outside of the housing, device, and subject.

The housing 210 further includes insertably removable elements 220A, 220B. Specifically, the elements 220A, 220B are magnets encapsulated in titanium housings, and these housings are adapted to snap into respective cavities in the housing 210 for both insertion and removal, along a direction that is parallel to a surgical plane of the housing. The surgical plane of the housing 210 is parallel to the XY plane illustrated in FIG. 2A.

The housing 210 may be made from biocompatible materials such as silicone and/or titanium.

FIG. 3 illustrates a pictorial view of a skull of a subject 311 with subcutaneous implants including the implantable device 200 of FIGS. 2A and 2B and a cochlear implant device 315. The surgical plane of the device 200, which is the XY plane shown, is approximately parallel to the skull at the position of implantation. This pictorial view illustrates the relatively small and straight, respective incisions (S1 307 and S2 309, blue straight lines) that are proximate and beside the implant location for insertion and/or removal of elements, in contrast with the more invasive and relatively larger arc incision (C 313, in blue) with a skin flap lift required for the cochlear implant. In one example for an embodiment device, each S (for "straight") incision 307, 309 is circa 10 mm long, whereas C 313 ("c-shaped" incision) is roughly 55 mm long. Nonetheless, for various embodiments, an element can be insertably removable with respect to the housing via an incision through a skin of a subject, wherein a length of the incision is less than or equal to 20 mm, 10 mm, or 5 mm, or wherein the length of the incision is in a range of 5 mm to 20 mm, and preferably 5 mm to 15 mm, or 7 mm to 13 mm.

In general, the smaller the incisions, the fewer complications arise from them; hence the two short straight incisions S are preferable to the larger curved incision C. Additionally, straight vertical incisions are preferred over c-shaped ones, as the blood vessels perfusing the scalp originate at the base of the skull and deploy themselves towards the top of the head, in an essentially vertical pattern. Therefore, by making straight vertical incisions for inserting and removing elements of embodiments devices, the likelihood of cutting across a blood vessel may be reduced. Cutting across a blood vessel would lead to a reduction of the blood supply of the scalp distal to the incision. Thus, embodiment devices are not only easier to service, they are also significantly safer than existing cochlear implants.

FIG. 4 is a flow diagram illustrating an embodiment procedure 400 for servicing an implantable device. At 431, at an incision proximate an implant location of the implantable device, the implantable device comprising a low-profile housing having a cavity defined in a side thereof and an element having a first portion adapted to be received in the housing cavity and a second portion adapted to protrude from the housing, insertably and removably accessing the element in a direction substantially parallel to a surgical plane of the implantable device. In one procedure within the scope of embodiments, wherein only one element of an implantable device needs to be serviced, only 431 is performed. Nonetheless, procedure 400 includes servicing additional elements of an embodiment device, as illustrated at 433.

At 433, the cavity is considered to be a first cavity, the side is considered to be a first side, the element is considered to be a first element, and the incision is considered to be a first incision. The method further includes accessing at one or more respective second incisions proximate the implant location of the implantable device. The low-profile housing can have one or more respective second cavities defined in the first side or in one or more respective second sides thereof. The implantable device can include one or more second elements having respective first portions adapted to be received in the housing cavity. The accessing is particularly insertably and removably accessing the one or more second elements in one or more respective second directions substantially parallel to the surgical plane, as will be understood in relation to the description of other embodiments herein.

In some embodiments of the method, the second portion includes at least one surface adapted for engagement with a surgical instrument for insertion and removal of the element with respect to the housing. The method may further be modified to utilize, employ, or operate upon any of the features of embodiments described above.

It will be understood that the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") when used herein, specify the presence of stated features, integers, steps, operations, elements, and/or components, but do not preclude the presence or addition of one or more other features, integers, steps, operations, elements, components, and/or groups thereof.

It will be further understood that, although the terms first, second, third, etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section without departing from the teachings of the present application.

It will be further understood that when an element is referred to as being "on", "attached", "connected" or "coupled" to another element, it can be directly on or above, or connected or coupled to, the other element, or one or more intervening elements can be present. In contrast, when an element is referred to as being "directly on", "directly attached", "directly connected" or "directly coupled" to another element, there are no intervening elements present. Other words used to describe the relationship between elements should be interpreted in a like fashion (e.g. "between" versus "directly between", "adjacent" versus "directly adjacent", etc.).

It will be further understood that when a first element is referred to as being "in", "on" and/or "within" a second element, the first element can be positioned: within an internal space of the second element, within a portion of the second element (e.g. within a wall of the second element); positioned on an external and/or internal surface of the second element; and combinations of one or more of these.

As used herein, the term "proximate", when used to describe proximity of a first component or location to a second component or location, is to be taken to include one or more locations near to the second component or location, as well as locations in, on and/or within the second component or location. For example, a component positioned proximate an anatomical site (e.g. a target tissue location), shall include components positioned near to the anatomical site, as well as components positioned in, on and/or within the anatomical site.

Spatially relative terms, such as "beneath", "below", "lower", "above", "upper" and the like may be used to describe an element and/or feature's relationship to another element(s) and/or feature(s) as, for example, illustrated in the figures. It will be further understood that the spatially relative terms are intended to encompass different orientations of the device in use and/or operation in addition to the orientation depicted in the figures. For example, if the device in a figure is turned over, elements described as "below" and/or "beneath" other elements or features would then be oriented "above" the other elements or features. The device can be otherwise oriented (e.g. rotated 90 degrees or at other orientations) and the spatially relative descriptors used herein interpreted accordingly.

The term "and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

As used herein, the term "functional element" is to be taken to include one or more elements constructed and arranged to perform a function. A functional element can comprise a sensor and/or a transducer. In some embodiments, a functional element is configured to deliver energy and/or otherwise treat tissue (e.g. a functional element configured as a treatment element). Alternatively or additionally, a functional element (e.g. a functional element comprising a sensor) can be configured to record one or more parameters, such as a subject physiologic parameter; a subject anatomical parameter (e.g. a tissue geometry parameter); a subject environment parameter; and/or a system parameter. In some embodiments, a sensor or other functional element is configured to perform a diagnostic function (e.g. to gather data used to perform a diagnosis). In some embodiments, a functional element is configured to perform a therapeutic function (e.g. to deliver therapeutic energy and/or a therapeutic agent). In some embodiments, a functional element comprises one or more elements constructed and arranged to perform a function selected from the group consisting of: deliver energy; extract energy (e.g. to cool a component); deliver a drug or other agent; manipulate a system component or subject tissue; record or otherwise sense a parameter such as a subject physiologic parameter or a system parameter; and combinations of one or more of these.

The term "transducer" where used herein is to be taken to include any component or combination of components that receives energy or any input, and produces an output. For example, a transducer can include an electrode that receives electrical energy, and distributes the electrical energy to tissue (e.g. based on the size of the electrode). In some configurations, a transducer converts an electrical signal into any output, such as light (e.g. a transducer comprising a light emitting diode or light bulb), sound (e.g. a transducer comprising a piezo crystal configured to deliver ultrasound energy), pressure, heat energy, cryogenic energy, chemical energy; mechanical energy (e.g. a transducer comprising a motor or a solenoid), magnetic energy, and/or a different electrical signal (e.g. a Bluetooth or other wireless communication element). Alternatively or additionally, a transducer can convert a physical quantity (e.g. variations in a physical quantity) into an electrical signal. A transducer can include any component that delivers energy and/or an agent to tissue, such as a transducer configured to deliver one or more of: electrical energy to tissue (e.g. a transducer comprising one or more electrodes); light energy to tissue (e.g. a transducer comprising a laser, light emitting diode and/or optical component such as a lens or prism); mechanical energy to tissue (e.g. a transducer comprising a tissue manipulating element); sound energy to tissue (e.g. a transducer comprising a piezo crystal); chemical energy; electromagnetic energy; magnetic energy; and combinations of one or more of these.

As used herein, the term "fluid" can refer to a liquid, gas, gel, or any flowable material, such as a material which can be propelled through a lumen and/or opening.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination. For example, it will be appreciated that all features set out in any of the claims (whether independent or dependent) can be combined in any given way.

It is to be understood that at least some of the figures and descriptions of the invention have been simplified to focus on elements that are relevant for a clear understanding of the invention, while eliminating, for purposes of clarity, other elements that those of ordinary skill in the art will appreciate may also comprise a portion of the invention. However, because such elements are well known in the art, and because they do not necessarily facilitate a better understanding of the invention, a description of such elements is not provided herein.

The teachings of all patents, published applications and references cited herein are incorporated by reference in their entirety.

While example embodiments have been particularly shown and described, it will be understood by those skilled in the art that various changes in form and details may be made therein without departing from the scope of the embodiments encompassed by the appended claims.

What is claimed is:

1. An implantable device comprising:
   a low-profile housing having a width and length extending in X and Y directions of an XY surgical plane of the implantable device, the width and length being greater than a height of the housing, the height of the housing extending in a subcutaneous Z direction perpendicular to the XY surgical plane, the housing having a cavity defined in a side thereof;
   an implantable element insertably removable with respect to the cavity in the side of the housing in a direction substantially parallel to the XY surgical plane of the implantable device, the element having a first portion adapted to be received in the housing cavity; and
   a second portion adapted to protrude from the housing upon insertion of the element into the housing cavity, the second portion being a distal end of the element that includes a flat surface with a detent hole extending therein adapted for engagement with a surgical instrument for insertion and removal of the element with respect to the housing, the second portion having a length which protrudes from the housing that is less than a length of the first portion which is received in the housing cavity, and exposes the detent hole, wherein the element includes one of a magnet, a battery, a sensor, an electronic module, an RFID tag, and a resorbable material.

2. The device of claim 1, further including an electronic circuit within the housing.

3. The device of claim 2, wherein the element is configured to have an electrical coupling to the electronic circuit.

4. The device of claim 1 wherein the element includes a radio-opaque marker.

5. The device of claim 1 wherein the element includes a consumable material.

6. The device of claim 1 wherein the housing and element are composed of biocompatible materials.

7. The device of claim 1 wherein the first portion is adapted to be friction fit into the housing cavity.

8. The device of claim 1 wherein the housing cavity includes a cavity wall and the first portion and the cavity wall are keyed to each other for engagement and alignment.

9. The device of claim 1 wherein the element is insertably removable with respect to the housing via an incision through a skin of a subject, wherein a length of the incision is less than or equal to 20 mm, 10 mm, or 5 mm, or wherein the length of the incision is in a range of 5 mm to 20 mm, 5 mm to 15 mm, or 7 mm to 13 mm.

10. The device of claim 1 wherein the cavity is a first cavity, the side is a first side, and the element is a first element, the device further comprising one or more second cavities defined in the first side or in one or more respective second sides of the low-profile housing, the device further comprising one or more respective second elements insertably removable with respect to the housing in one or more respective second directions substantially parallel to the surgical plane of the implantable device, the one or more respective second elements having one or more respective first portions adapted to be received in the one or more respective second cavities.

* * * * *